United States Patent [19]

Holleman et al.

[11] 4,326,033

[45] Apr. 20, 1982

[54] MODIFIED UROKINASE HAVING EXTENDED ACTIVITY AND METHOD OF MAKING

[75] Inventors: William H. Holleman; Shaw-Guang Lee, both of Libertyville; Paul P. Hung, Waukegan, all of Ill.

[73] Assignee: Abbott Laboratories, North Chicago, Ill.

[21] Appl. No.: 146,823

[22] Filed: May 5, 1980

[51] Int. Cl.$^3$ .................. C12N 9/48; C12N 9/72
[52] U.S. Cl. ..................... 435/212; 435/215
[58] Field of Search ................ 435/212, 215

[56] References Cited

U.S. PATENT DOCUMENTS

| | | | |
|---|---|---|---|
| 3,930,944 | 1/1976 | Nicol | 435/215 |
| 3,950,223 | 4/1976 | Yugari et al. | 435/215 X |
| 4,061,538 | 12/1977 | Dorner et al. | 435/68 |
| 4,184,917 | 1/1980 | Dorner et al. | 435/68 |

OTHER PUBLICATIONS

Bose et al., Journal of Biological Chemistry, vol. 252, No. 23, pp. 8336-8337, Dec. 10, 1977.
Fujisawa et al., Journal of Biological Chemistry, vol. 253, pp. 8677-8679, Dec. 25, 1978.
Advances in Enzymology, vol. 41, pp. 99-128 (1974).

*Primary Examiner*—Lionel M. Shapiro
*Attorney, Agent, or Firm*—Gildo E. Fato; Robert L. Niblack

[57] ABSTRACT

Described is a structurally modified urokinase which is biologically active over an extended time period in comparison to native urokinase. The extended activity permits the administration of lower doses of urokinase when it is used in the treatment of thromboembolic diseases. Methods of appropriately modifying the structure of urokinase are described.

7 Claims, 1 Drawing Figure

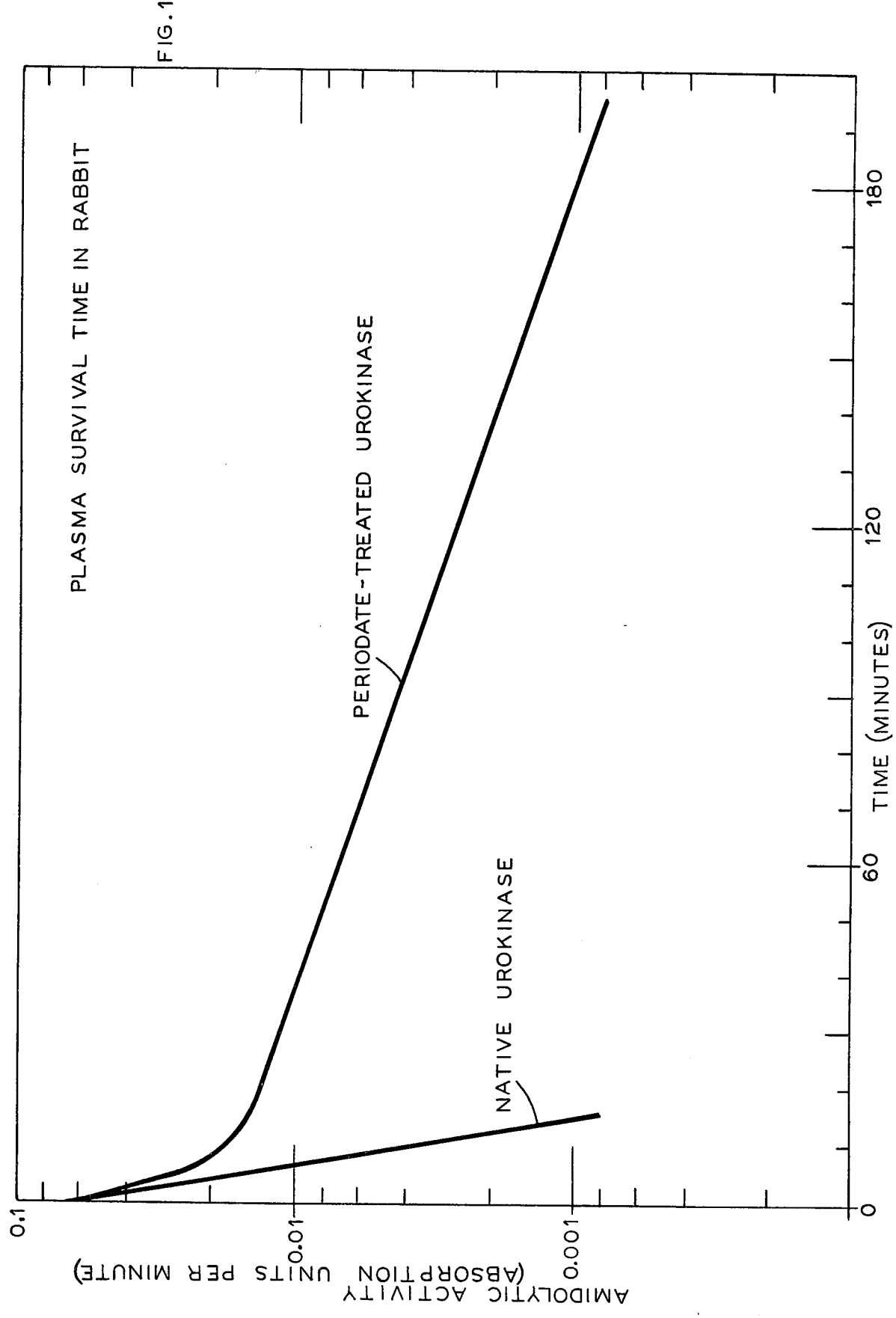

MODIFIED UROKINASE HAVING EXTENDED ACTIVITY AND METHOD OF MAKING

BACKGROUND OF THE INVENTION

Urokinase isolated from kidney tissue culture fluids is a glycoprotein and is one of the most promising fibrinolytic agents in the treatment of thromboembolic diseases. However, urokinase has a relatively short half-life of about 4 minutes when injected into experimental animals and about 8-30 minutes in man. This very short half-life has necessiated the usage of dosage schedule which requires large amounts of urokinase to be infused for a long period of time, in the range of 6-24 hours. Because of this, a structurally modified urokinase possessing a longer biological half-life would be very desirable.

Urokinase from human fetal kidney tissue culture has been purified to homogeneity and has a molecular weight of 32,000 and a specific activity of 250,000 units/mg. This material is a glycoprotein which contains 8% of carbohydrate with little or no sialic acid i.e., urokinase is an asialo-glycoprotein. Sialic acid is usually located at the terminals on the carbohydrate moiety of glycoproteins. It has been reported that sialylated glycoproteins display long plasma survival time following intravenous injection. On the other hand, asialo-glycoproteins with galactose or other non-reducing sugars exposed at the terminal are rapidly cleared from plasma by adsorptive pinocytosis via a liver hepatocyte recognition system as elucidated by Ashwell and colleagues (Ashwell, G., Morell, A., Adv. Enzymol. 41 99-128, 1974).

SUMMARY OF THE INVENTION

The present invention provides methods of modifying the carbohydrate structure in urokinase so that the half-life is increased while the fibrinolytic activity is not substantially decreased. Methods of modifying the urokinase structure are: (1) treatment of urokinase with enzymes which will specifically remove carbohydrate units; e.g. galactosidases, mannosidases, glucosidases, neuraminidases, and (2) Chemical treatment of the urokinase to remove or degrade the carbohydrate portion of the molecule.

DRAWING

FIG. 1 is a chart illustrating the plasma survival time of the modified urokinase of the present invention and native urokinase, in the rabbit.

DETAILED DESCRIPTION

The following examples illustrate the invention and establish the extended activity of the modified urokinase structure.

EXAMPLE 1

Periodate Oxidation

Periodate oxidation modifies sugars in glycoproteins. The oxidation method consisted of standard published procedures. (Biochem. Biophys. Res. Comm. 57 55. 1974). For example, one vial of urokinase (ABBOKINASE®), was dissolved in 3.0 ml. of 0.1 M sodium phosphate buffer, 0.15 NaCl, pH 6.0, and dialyzed against the same buffer overnight to remove manitol which was present in the original lypholyzed powder. The dialyzed urokinase solution was recovered in foil-wrapped test tube, and one-tenth volume of stock periodate solution (0.1 M) was added at 4° C. The oxidation was conducted in dark at the same temperature and small aliquots were removed during the course of reaction for activity assay using chromogenic substrate (Kabi code no. S-2444). After 70 minutes of oxidation, about 50% of the original activity stil remained. The oxidation reaction was then stopped by the addition of one-tenth volume of glycerol. Ethanolamine (2-fold molar excess of periodate concentration) was then added to form Schiffs' base with the aldehyde groups to prevent intermolecular cross-linkage. The final product was then dialyzed against normal saline and it contained 20% of the fibrinolytic activity of the original starting material.

EXAMPLE 2

Biological half-lives of native or modified urokinase

To determine the half-life of the native or the periodate-oxidized urokinase from example 1, rabbits having about 4 kg. body weight were used. The rabbits were canulated on one artery ear vein and 0.1 ml. heparin (100 USP unit/kg) was injected into the cathter to prevent blood clotting. Urokinase with a dosage of 20,000 Ploug units (U-3 units) per kg. body weight was injected into the lateral ear vein on the other side. Blood (0.9 ml.) was collected at 0.5, 1, 2, 4, 8 ... minutes after the urokinase injection from the canulated ear. Plasma separated from each blood sample was collected and urokinase activity determined. The plasma clearance profile of the native urokinase is shown in FIG. 1 (0—0). It gave a half-life of about 3.5 minutes. The intergrated time x activity area is 0.85 for the native urokinase. The profile of periodate-oxidized urokinase is also shown in FIG. 1 (x—x). During the first 3 hour period, it showed a biphasic profile. The first phase of the curve superimposed with that of the native urokinase, which had a time x activity area of 0.096. The second phase of the profile has a much longer half-life of about 40 minutes with some activity still present after 3 hours. The intergrated effective time x activity area of this second phase is 3.17, which is much bigger than that of the native urokinase (0.85).

What is claimed is:

1. A method of increasing the biological half-life of urokinase without substantially decreasing the fibrinolytic activity there of said method comprising treating urokinase to remove or degrade the carbohydrate portion of the molecule.

2. The method of claim 1 comprising enzymatically or chemically treating the urokinase.

3. The method of claim 2 wherein said chemical treatment comprises periodate oxidation of said carbohydrate portion of the molecule.

4. A method of modifying the carbohydrate portion of the urokinase molecule to thereby increase the biological half-life thereof, said method comprising:
   (a) dissolving a selected amount of urokinase in a buffer to obtain a solution,
   (b) dialyzing the urokinase solution against the same buffer to remove any mannitol which may be present,
   (c) adding periodate solution to the dialyzed urokinase to oxidize the carbohydrate portion thereof to form a modified urokinase, the oxidation reaction being conducted under dark conditions,
   (d) terminating the oxidation reaction, and (e) forming a Schiffs' base derivative of the modified urokinase by adding an amine to the modified urokinase to obtain a final product.

5. The method of claim 4 wherein the oxidation is conducted at a temperature below 10° C.

6. The method of claim 5 wherein the oxidation is conducted for a period of from 1 to 4 hours.

7. A structurally modified urokinase having a modified carbohydrate portion of the molecule and made by the method of claim 1, said structurally modified urokinase having substantial fibrinolytic activity.

* * * * *